United States Patent
Markwardt et al.

(10) Patent No.: US 12,285,162 B2
(45) Date of Patent: Apr. 29, 2025

(54) SYSTEMS AND METHODS FOR ROBOTIC ENDOLUMINAL SUTURING INSTRUMENT

(71) Applicant: Noah Medical Corporation, San Jose, CA (US)

(72) Inventors: Neil Markwardt, Redwood City, CA (US); Matthew Robert Penny, Holly Springs, NC (US); Daniel Nasr-Church, San Diego, CA (US); Julia Toye, San Francisco, CA (US); Benjamin Selle, Fremont, CA (US)

(73) Assignee: Noah Medical Corporation, San Carlos, CA (US)

( * ) Notice: Subject to any disclaimer, the term of this patent is extended or adjusted under 35 U.S.C. 154(b) by 0 days.

(21) Appl. No.: 18/894,964

(22) Filed: Sep. 24, 2024

(65) Prior Publication Data
US 2025/0009351 A1    Jan. 9, 2025

Related U.S. Application Data

(63) Continuation of application No. PCT/US2024/018867, filed on Mar. 7, 2024.

(60) Provisional application No. 63/489,258, filed on Mar. 9, 2023.

(51) Int. Cl.
*A61B 17/04* (2006.01)
*A61B 17/062* (2006.01)
*A61B 34/30* (2016.01)
*A61B 17/00* (2006.01)

(52) U.S. Cl.
CPC ...... *A61B 17/0469* (2013.01); *A61B 17/0482* (2013.01); *A61B 17/0625* (2013.01); *A61B 34/30* (2016.02); *A61B 2017/0046* (2013.01); *A61B 2034/303* (2016.02)

(58) Field of Classification Search
CPC ............. A61B 17/062; A61B 17/0625; A61B 2017/047; A61B 2034/301; A61B 2034/305; A61B 2034/306
See application file for complete search history.

(56) References Cited

U.S. PATENT DOCUMENTS

| | | | |
|---|---|---|---|
| 2006/0178556 A1 | 8/2006 | Hasser et al. | |
| 2010/0152751 A1* | 6/2010 | Meade | A61B 34/30 606/144 |
| 2010/0262165 A1* | 10/2010 | Kirsch | A61B 17/0469 606/144 |
| 2012/0143222 A1* | 6/2012 | Dravis | A61B 17/0469 606/145 |
| 2012/0277768 A1 | 11/2012 | Viola et al. | |
| 2018/0242967 A1 | 8/2018 | Meade | |
| 2018/0280016 A1* | 10/2018 | Krespi | A61B 17/0469 |

(Continued)

OTHER PUBLICATIONS

PCT/US2024/018867 International Search Report and Written Opinion dated Sep. 3, 2024.

*Primary Examiner* — Martin T Ton
(74) *Attorney, Agent, or Firm* — WILSON SONSINI GOODRICH & ROSATI

(57) ABSTRACT

A suturing instrument is provided. The suturing instrument comprises: a flexible shaft comprising an articulatable bending section; and a needle end effector located at a distal end of the bending section. The needle end effector comprises a toggle-based rotation mechanism to switch an orientation of a needle to engage and disengage the needle with a ferrule.

20 Claims, 17 Drawing Sheets

(56) References Cited

U.S. PATENT DOCUMENTS

| | | | |
|---|---|---|---|
| 2019/0059877 A1* | 2/2019 | Mumaw | A61B 17/0469 |
| 2019/0231343 A1* | 8/2019 | Sauer | A61B 17/0482 |
| 2019/0254653 A1 | 8/2019 | Raybin et al. | |
| 2019/0298465 A1* | 10/2019 | Chin | A61B 17/3201 |
| 2020/0360011 A1 | 11/2020 | Deuel et al. | |
| 2021/0369263 A1* | 12/2021 | Bosworth | A61B 17/0469 |
| 2022/0265267 A1* | 8/2022 | Parker | A61B 17/0469 |
| 2023/0065020 A1 | 3/2023 | Jiang | |

\* cited by examiner

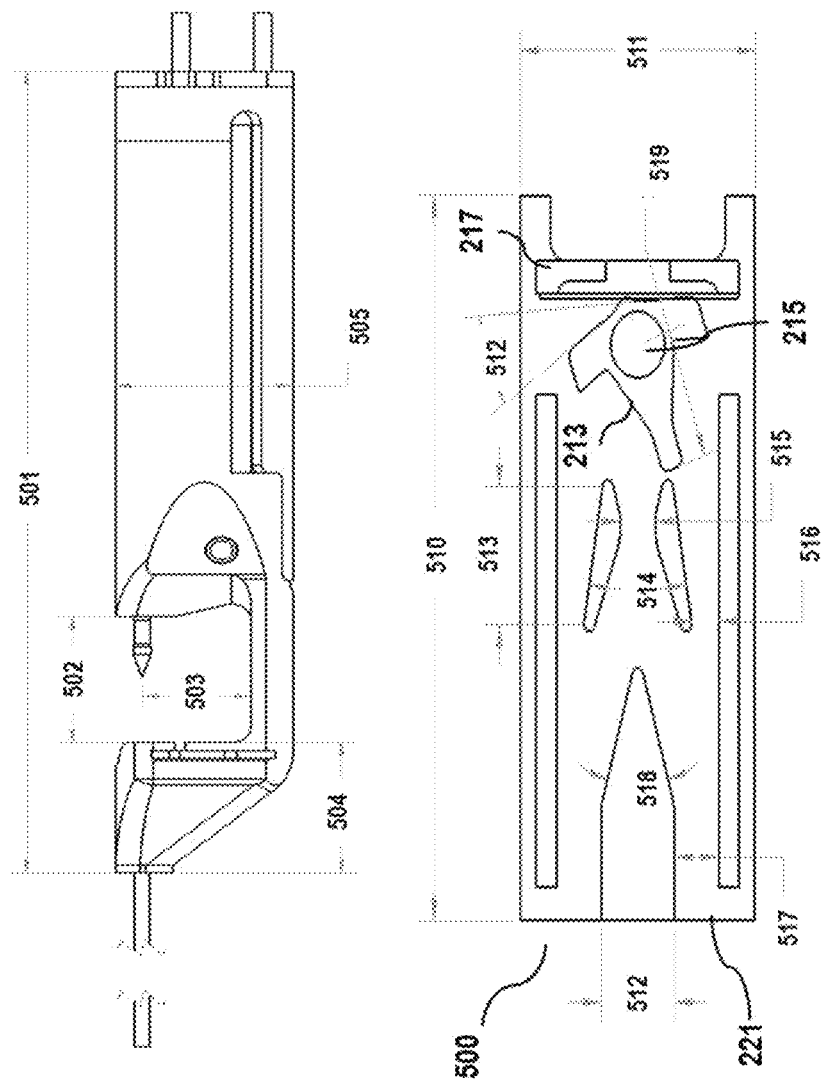

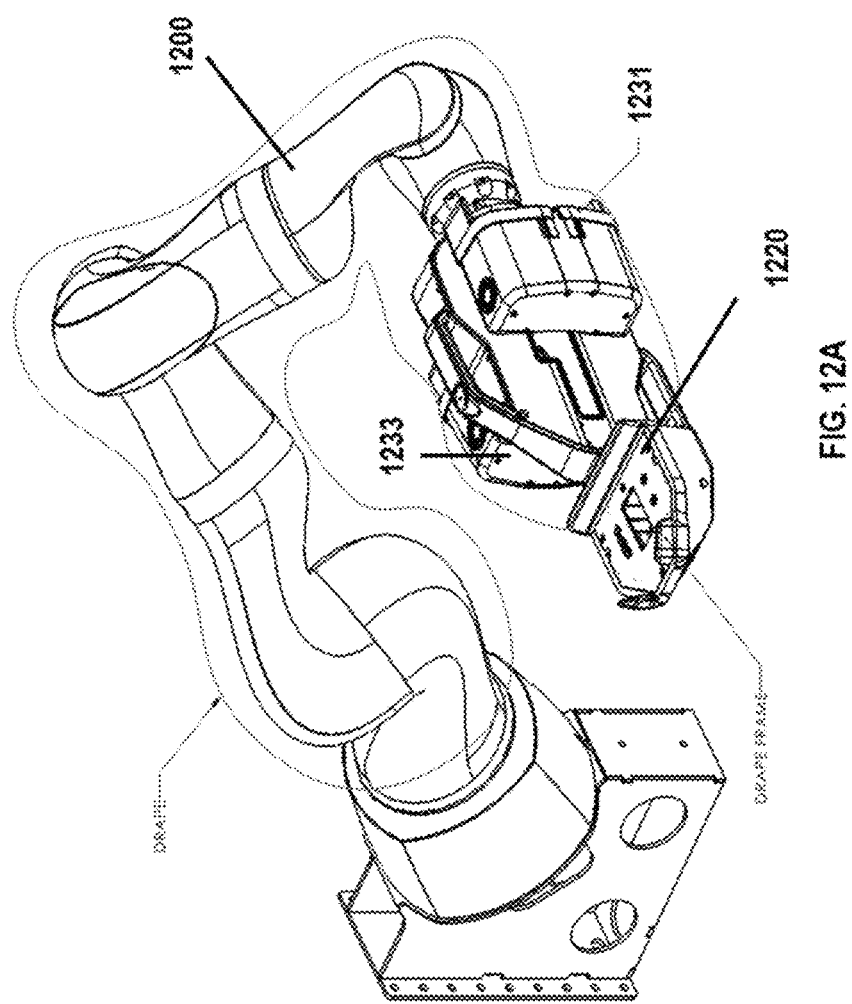

SYSTEMS AND METHODS FOR ROBOTIC ENDOLUMINAL SUTURING INSTRUMENT

CROSS-REFERENCE

This application is a continuation of International Application No. PCT/US2024/018867, filed Mar. 7, 2024, which claims priority to U.S. Provisional Patent Application No. 63/489,258, filed on Mar. 9, 2023, which is entirely incorporated herein by reference.

BACKGROUND

Endoscopy procedures use an endoscope to examine the interior of a hollow organ or cavity of the body. Unlike many other medical imaging techniques, endoscopes are inserted into the organ directly via the mouth or other naturally occurring orifices. Flexible endoscopes that can deliver instinctive steering and control are useful in diagnosing and treating diseases that are accessible through any natural orifice in the body. Depending on the clinical indication, the endoscope may be designated as colonoscope, gastroscope, bronchoscope, ureteroscope, ENT scope, and various others. For example, a flexible colonoscope may be intubated to transverse colon for diagnosis and/or surgical treatment.

Endoscopes are traditionally made to be re-usable, which may require thorough cleaning, dis-infection, and/or sterilization after each procedure. In most cases, cleaning, dis-infection, and sterilization may be aggressive processes to kill germs and/or bacteria. Such procedures may also be harsh on the endoscopes themselves. Therefore, the designs of such re-usable endoscopes can often be complicated, especially to ensure that the endoscopes can survive such harsh cleaning, dis-infection, and sterilization protocols. Periodical maintenance and repairs for such re-usable endoscopes may often be needed.

Low cost, disposable medical devices designated for a single-use have become popular for instruments that are difficult to clean properly. Single-use, disposable devices may be packaged in sterile wrappers to avoid the risk of pathogenic cross-contamination of diseases such as HIV, hepatitis, and other pathogens. Hospitals generally welcome the convenience of single-use disposable products because they no longer have to be concerned with product age, overuse, breakage, malfunction, and sterilization. Traditional endoscopes often include a handle that operators use to maneuver the endoscope. For single-use endoscopes, the handle usually encloses the camera, expensive electronics, and mechanical structures at proximal end in order to transmit the video and allow the users to maneuver the endoscope via a user interface. This may lead to high cost of the handle for a single-use endoscope.

An endoscope device may have a working channel allowing tools such as graspers, cutters or suturing instruments to pass through. In another example, a suturing device can be coupled to the distal end of an endoscope, which enables suturing in the gastroesophageal tract of a patient. However, current suturing devices are designed for manual endoscope devices such as laparoscopy. It is desirable to clinicians to provide suturing devices suitable for robotic endoscopic platforms or used endoluminally with reduced size and improved motion control.

In an aspect of the present disclosure, a suturing instrument is provided. The suturing instrument comprises: a flexible shaft comprising an articulatable bending section; and a needle end effector located at a distal end of the articulatable bending section, where the needle end effector comprises a toggle-based rotation mechanism to switch an orientation of a needle to engage and disengage the needle with a ferrule.

In some embodiments, the needle is rotated back and forth over a predetermined range of angle with respect to an axial axis to switch the orientation. In some cases, the predetermined range of angle is about 60°. In some embodiments, the toggle-based rotation mechanism comprises a plate formed with a plurality of channels to guide the switching the orientation of the needle. In some cases, the plurality of channels are formed on a substantially flat surface of the plate. In some cases, the toggle-based rotation mechanism comprises a spring biased toggle to switch the needle from a channel oblique to an axial axis of the needle end effector to a channel parallel to the axial axis of the needle end effector. In some embodiments, the toggle-based rotation mechanism comprises an antagonistic cable to drive a forward and backward motion of the needle.

In some embodiments, a length of the needle end effector is not greater than 30 mm. In some embodiments, a diameter of the needle end effector is not greater than 5 mm. In some embodiments, the needle end effector is rotatable relative to the articulatable bending section. Alternatively, the needle end effector is fixedly coupled to the articulatable bending section.

In some embodiments, the articulable bending section is actuated by one or more pull wires and a proximal end of the one or more pull wires are coupled to a handle of the suturing instrument. In some cases, a cable driving a translational motion of the needle is coupled to the handle. In some cases, the handle is releasably coupled to a robotic support via a first instrument driving mechanism. In some cases, the first instrument driving mechanism drives an articulation motion of the articulable bending section and an operation of the needle end effector.

In some embodiments, the suturing instrument is inserted through a working channel of a flexible robotic endoscope. In some cases, the flexible robotic endoscope comprises an articulable bending section. In some instances, the flexible robotic endoscope is releasably coupled to a robotic support via a second instrument driving mechanism. For example, the articulable bending section is actuated by the second instrument driving mechanism.

In another aspect, a robotic endoluminal suturing instrument is provided. The robotic endoluminal suturing instrument comprises: a flexible shaft comprising an articulatable bending section, where an articulating motion of the articulatable bending section is driven by one or more pull wires; a needle end effector coupled to a distal end of the articulable bending section, where the needle end effector comprises a needle driven by a cable to translate and rotate to engage and disengage with a ferrule; and a handle configured to releasably couple the robotic endoluminal suturing instrument to an instrument driving mechanism, where the instrument driving mechanism actuates the one or more pull wires and the cable.

In some embodiments, a length of the needle end effector is not greater than 30 mm. In some embodiments, a diameter of the needle end effector is not greater than 5 mm.

In some embodiments, the needle end effector is rotatable relative to the articulatable bending section. In some embodiments, the needle end effector is fixedly coupled to the articulatable bending section. In some embodiments, the needle is rotated back and forth over a predetermined range of angle with respect to an axial axis to switch an orientation of the needle. In some cases, the predetermined range of angle is about 60°.

In some embodiments, the needle end effector comprises a toggle-based rotation mechanism to switch an orientation of the needle. In some cases, the toggle-based rotation mechanism comprises a plate formed with a plurality of channels to guide the switching the orientation of the needle. In some instances, the plurality of channels are formed on a substantially flat surface of the plate.

In some embodiments, the robotic endoluminal suturing instrument is inserted through a working channel of a flexible robotic endoscope. In some cases, the flexible robotic endoscope comprises an articulable bending section and is releasably coupled to a robotic support.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein), of which:

FIG. 5A and FIG. 5B show examples of a needle end effector with a compact design.

FIG. 12A and FIG. 12B show an example of an instrument driving mechanism (IDM) providing mechanical interface to the handle portion of the robotic endoscope.

DETAILED DESCRIPTION

Figure 1:
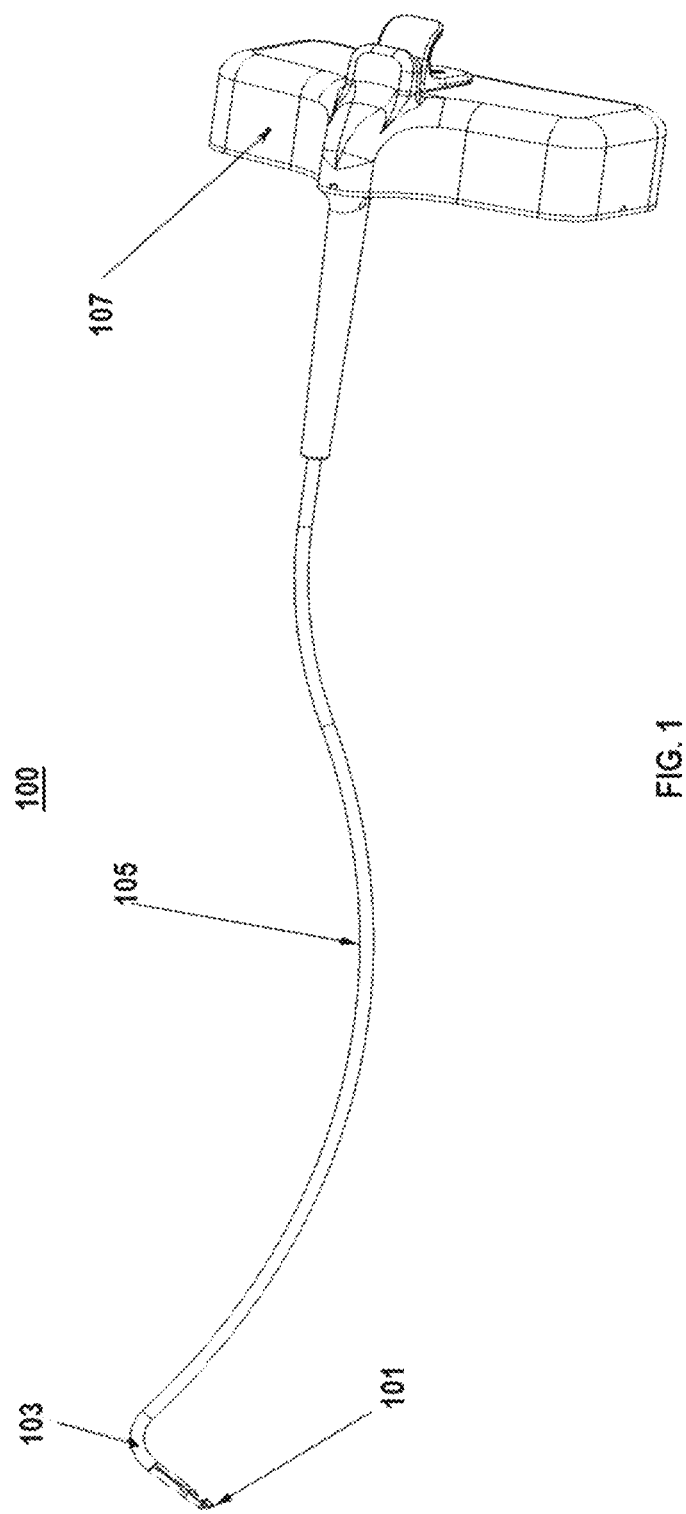
FIG. 1 schematically shows an example of a suturing instrument.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The embodiments disclosed herein can be combined in one or more of many ways to provide improved diagnosis and therapy to a patient. The disclosed embodiments can be combined with existing methods and apparatus to provide improved treatment, such as combination with known methods of pulmonary diagnosis, surgery and surgery of tissues and organs, for example. It is to be understood that any one or more of the structures and steps as described herein can be combined with any one or more additional structures and steps of the methods and apparatus as described herein, the drawings and supporting text provide descriptions in accordance with embodiments.

While exemplary embodiments will be primarily directed at a suturing device or system for colonoscope or gastroscope, one of skill in the art will appreciate that this is not intended to be limiting, and the devices described herein may be used for other therapeutic or diagnostic procedures and in various anatomical regions of a patient's body. The provided suturing device or system can be utilized in urology, gynecology, rhinology, otology, laryngoscopy, gastroenterology with the endoscopes, combined devices including endoscope and instruments, endoscopes with localization functions, one of skill in the art will appreciate that this is not intended to be limiting, and the devices described herein may be used for other therapeutic or diagnostic procedures and in other anatomical regions of a patient's body, such as such as brain, heart, lungs, intestines, eyes, skin, kidney, liver, pancreas, stomach, uterus, ovaries, testicles, bladder, ear, nose, mouth, soft tissues such as bone marrow, adipose tissue, muscle, glandular and mucosal tissue, spinal and nerve tissue, cartilage, hard biological tissues such as teeth, bone and the like, as well as body lumens and passages such as the sinuses, ureter, colon, esophagus, lung passages, blood vessels and throat, and various others, in the forms of: BronchoScope, Neuroendo-Scope, EncephaloScope, OphthalmoScope, OtoScope, RhinoScope, LaryngoScope, GastroScope, EsophagoScope, BronchoScope, ThoracoScope, PleuroScope, AngioScope, MediastinoScope, NephroScope, GastroScope, DuodenoScope, CholeodoScope, CholangioScope, LaparoScope, AmioScope, UreteroScope, HysteroScope, CystoScope, ProctoScope, ColonoScope, ArthroScope, SialendoScope, Orthopedic Endoscopes, and others, in combination with various tools or instruments.

The systems and apparatuses herein can be combined in one or more of many ways to provide improved diagnosis and therapy to a patient. Systems and apparatuses provided herein can be combined with existing methods and apparatus to provide improved diagnosis, surgery operations of various tissues and organs, for example. It is to be understood that any one or more of the structures and steps as described herein can be combined with any one or more additional structures and steps of the methods and apparatus as described herein, the drawings and supporting text provide descriptions in accordance with embodiments.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, the terms distal and proximal may generally refer to locations referenced from the apparatus, and can be opposite of anatomical references. For example, a distal location of a primary shaft or catheter may correspond to a proximal location of an elongate member of the patient, and a proximal location of the primary sheath or catheter may correspond to a distal location of the elongate member of the patient.

Suturing Instrument

FIG. 1 schematically shows an example of a suturing instrument 100. The suturing instrument 100 may comprise an end effector 101 located at a distal end of an elongate member. The elongate member may be an articulatable, flexible member comprising a bending section 103, a flexible shaft 105 and a proximal end 107. The proximal end 107 may be a handle that is releasably attached to a robotic support. In some cases, the proximal end 107 may comprise driving components (e.g., pulley) that are releasably coupled to an instrument driving mechanism to drive an operation of the end effector (e.g., needle operation, roll movement, etc.) and/or the motion (e.g., articulation) of the bending section 103.

Figure 12B:
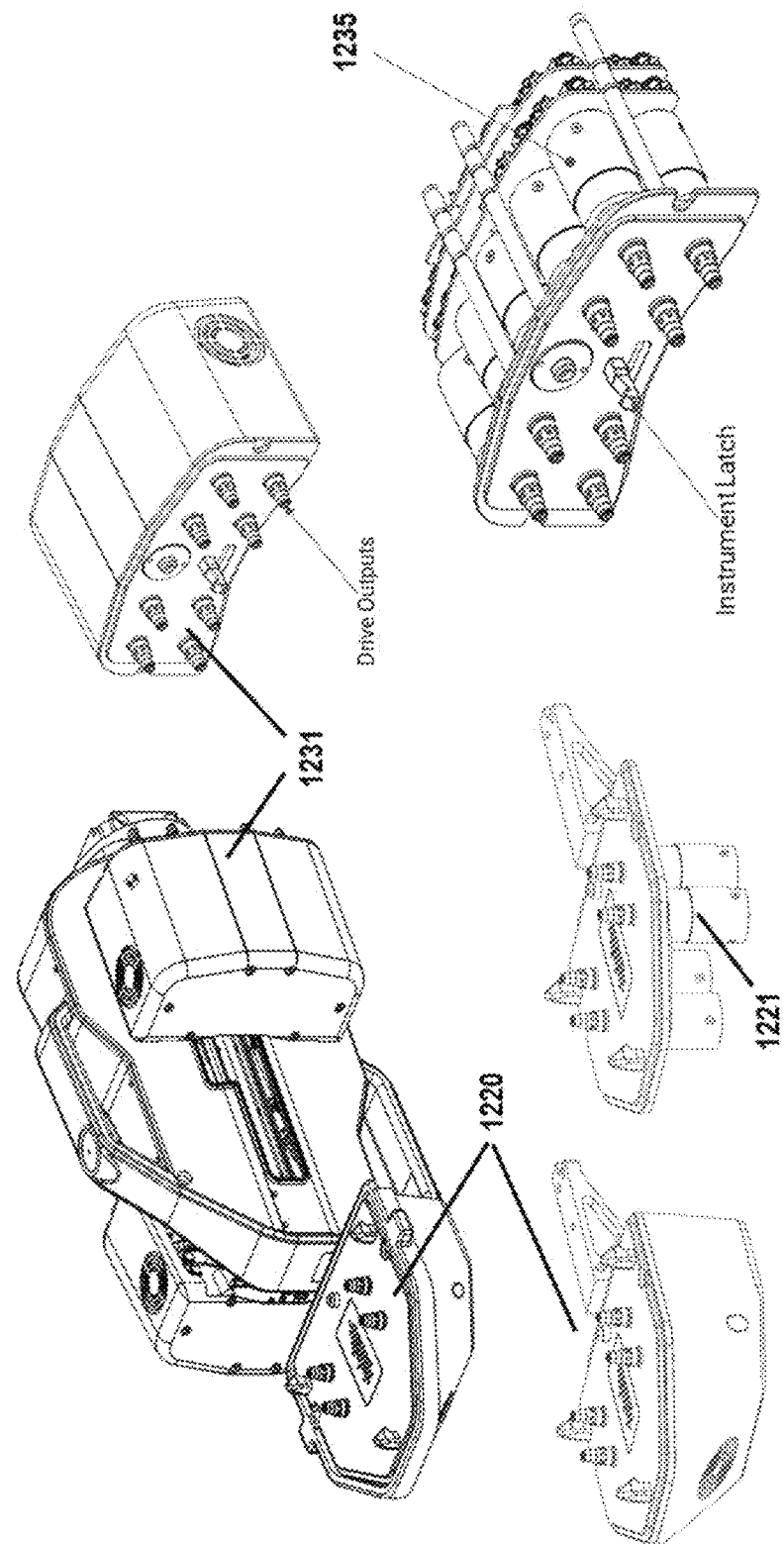

In some cases, the proximal end 107 may comprise a mechanical interface to allow the suturing instrument to be releasably coupled to an instrument driving mechanism attached to a robotic support or a hand-held controller. The instrument driving mechanism (IDM) can be the same as the IDM 1231, 1233 as illustrated in FIG. 12A and FIG. 12B. The IDM may comprise a set of motors 1235 that are actuated to rotationally drive a set of pull wires of the elongate member. The proximal end 107 may be mounted onto the instrument drive mechanism 1231 or 1233 so that its pulley/capstans assemblies are driven by the set of motors. The number of pulleys may vary based on the pull wire configurations. In some cases, one, two, three, four, or more pull wires may be utilized for articulating the flexible suturing instrument and for driving the motion of the needle end effector. In some cases, one pull wire may be coupled to and driven by a pulley. In some cases, more than one wires may be coupled to a driven pulley. For example, two or more wires may be coupled to the same driven pulley antagonistically to drive the needle end effector motion such that rotation of the pulley provides tension to one wire(s) while slacking the other(s).

The bending section 103 may be articulated in two or more degrees of freedom. The articulation of the bending section 103 may be controlled by applying force to the distal tip portion via the one or multiple pull wires. A distal end of the one or more pull wires may be attached to the distal end of the suturing instrument 100. In the case of multiple pull wires, pulling one wire at a time may change the orientation of the end effector 101 to pitch up, down, left, right or any direction needed. In some cases, the pull wires may be anchored at the distal tip portion of the suturing instrument 100, running through the bending section, and entering the proximal end they are coupled to a driving component (e.g., pulley). This pulley may interact with an output shaft from the robotic system. In some cases, one or more of the pull wires may be utilized as the needle drive mechanism (e.g., needle retraction cable and needle insertion cable in FIG. 2) to drive forward and backward motion of the needle in the end effector.

In some embodiments, the proximal end or portion of one or more pull wires may be operatively coupled to various mechanisms (e.g., gears, pulleys, capstans, etc.) in the proximal end. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the suturing instrument 100, such that operation of the pull wires by the control unit may apply force or tension to the distal portion which may steer or articulate (e.g., up, down, pitch, yaw, or any direction in-between) at least the distal portion (e.g., flexible section) of the suturing instrument. The pull wires may be made of any suitable material such as stainless steel (e.g., SS316), metals, alloys, polymers, nylons or biocompatible material. In some embodiments, different pull wires may be made of different materials for varying the load bearing capabilities of the pull wires.

Figure 14:
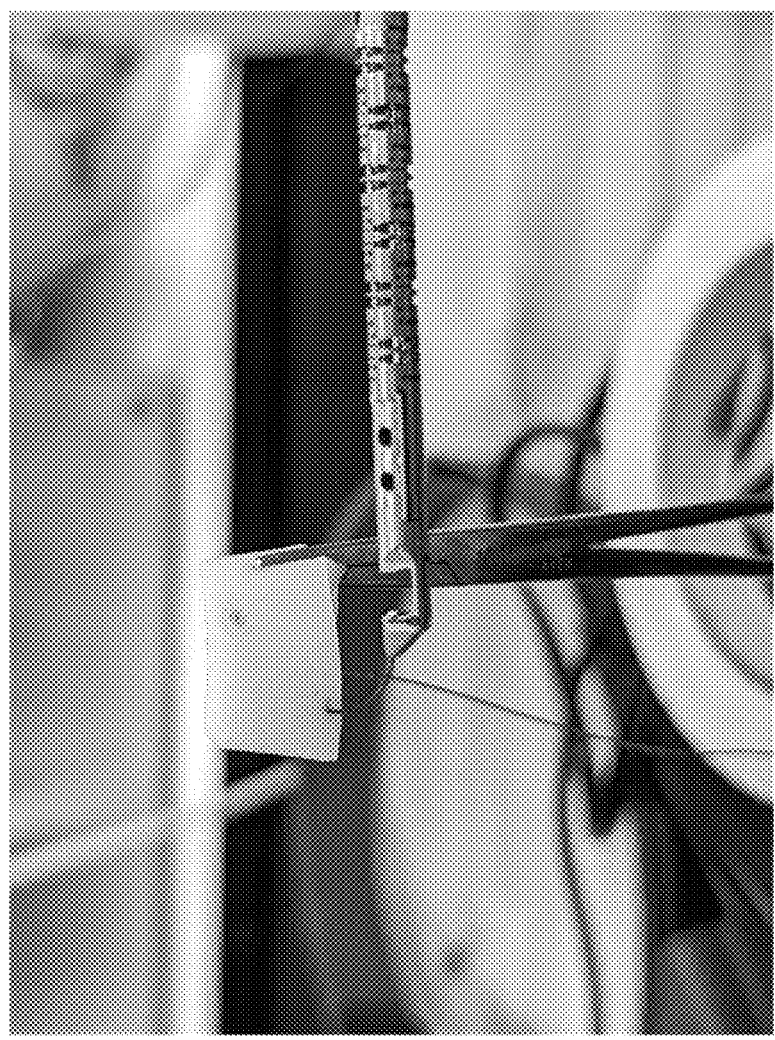
FIG. 14 shows an example of an end effector controlled to perform suturing operations.

The end effector 101 may comprise a needle device. The needle device may be attached to the distal portion of the suturing instrument 100. The needle device may have two (e.g., roll and translation), three (e.g., roll and articulation), four (e.g., roll, articulation and translation) or more degrees of freedom. For example, the needle device may have a roll movement (e.g., rotatable about the longitudinal axis of the elongate member), articulatable about two axes (e.g., via the articulation of the bending section) and may have translational movement (e.g., insertion and retraction of the device). In some cases, the roll movement of the needle device may be achieved via a wrist at the distal portion of the suturing instrument such that the needle device 101 may have a roll movement relative to the elongate member. Alternatively, the needle device may be integrated to or fixedly coupled to the distal portion of the bending section 103 and may not have roll movement relative to the bending section. In some cases, the roll movement of the needle device may be achieved via the roll movement of the elongate member, a wrist located at the distal end of the bending section 103 or a combination of both. FIG. 14 shows an example of the end effector controlled to perform suturing operations.

The present disclosure provides a novel needle device or needle end effector with reduced size and improved operation control that can be used with an endoscope or colonoscope to perform operations related to suturing such as needle introduction and retrieval as well as needle throwing during upper and lower gastrointestinal (GI) tract endoscopy, gastric endoscopy, small bowel endoscopy or other procedures. The reduced size of the end effector may beneficially ease insertion, manipulation, and retraction of an endoscope during colonoscopy. In particular, the devices and methods of the present disclosure provides an improved needle device with a novel and unique needle rotation cycle allowing for a precise needle operation control for robotic endoluminal surgical platforms.

Current needle devices may achieve a stitch cycle including traversing a needle, picking up a ferrule, the ferrule being returned to its ferrule compartment and the ferrule being stripped. Existing needle devices may rotate the needle into various angles in order to engage and disengage the needle tip with the ferrule. For example, by orienting a faceted edge of a needle, the faceted edge may engage and release from a ferrule latch. However, existing needle devices may have a continuous rotation or rotary movement (e.g., a rotating cam with slots to engage with a rod) that may be difficult for manufacturing (e.g., high cost to fabricate the rotating cam) and may not have a compact size. It is desirable to provide an improved mechanism for engaging and disengaging the needle and ferrule that is suitable for automated robotic control with reduced dimension and easy manufacture.

The needle instrument of the present disclosure may provide an improved mechanism for driving the needle rotation cycles. In some embodiments, the needle may be rotated at predefined angles back and forth within a suturing cycle. Unlike the existing methods which drive the needle to continuously rotate in one direction, the provided needle instrument may provide a toggle-based rotation indexing mechanism to change the needle rotation on alternating cycles of the device thereby providing precise indexed control of operation.

In some embodiments, the automated robotic needle operation may include a suture cycle and a reset cycle. In some cases, a complete stitch cycle may comprise alternating cycles including a suture cycle and a reset cycle. The needle operation may repeat the suture cycle and reset cycle in alternating fashion to perform stitches. During a suture cycle, the needle may advance or extend from an initial state, pierce tissue, dock with a ferrule, then retract drawing suture through the tissue. During a reset cycle, the needle may advance or extend to place the ferrule back in a pocket, then retract leaving the ferrule in the pocket.

An orientation of the needle may be changed on the alternating cycles. In some embodiments, the needle may be rotated back and forth (e.g., clockwise and counterclockwise) about the longitudinal axis between the suture cycle and the reset cycle. For instance, in a first stitch cycle, the needle may be first oriented to a dock orientation in a suture cycle and rotated to a strip orientation in the reset cycle. At the end of the reset cycle, the needle is rotated back (i.e., in the opposite direction) to the initial orientation (dock orientation) to prepare the needle for the subsequent stitch cycle (i.e., second stitch cycle).

Figure 7:
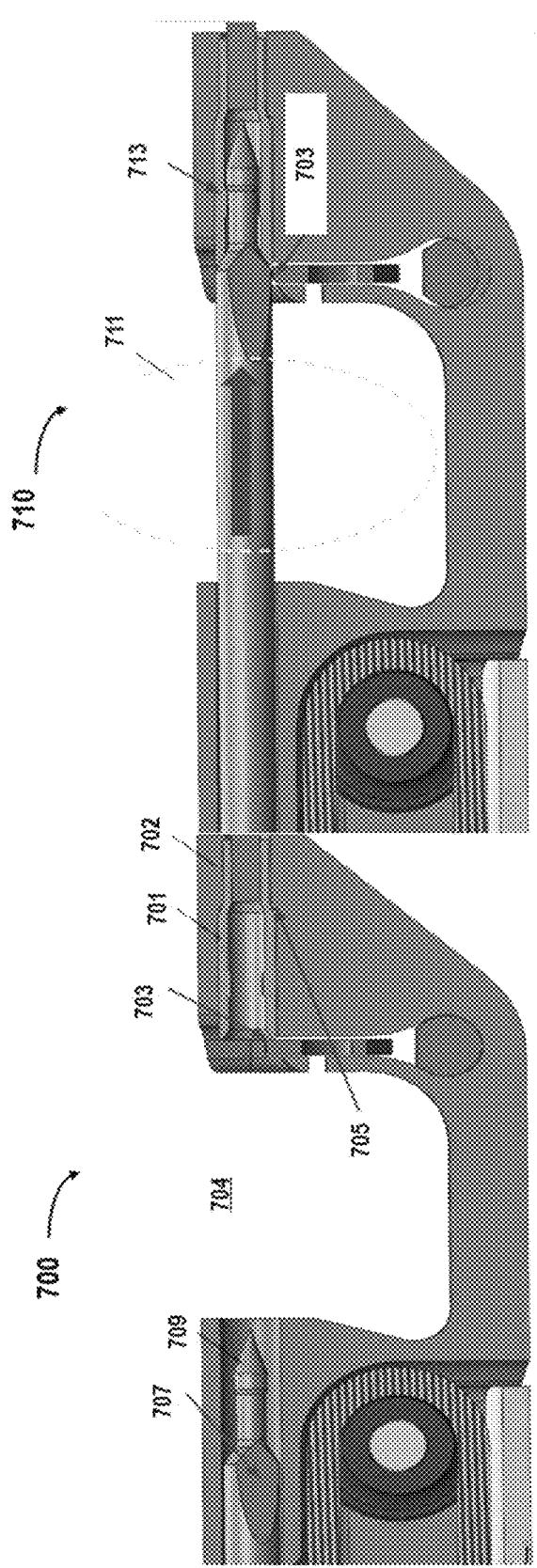
FIG. 7 and FIG. 8 schematically show a suturing cycle.
Figure 8:
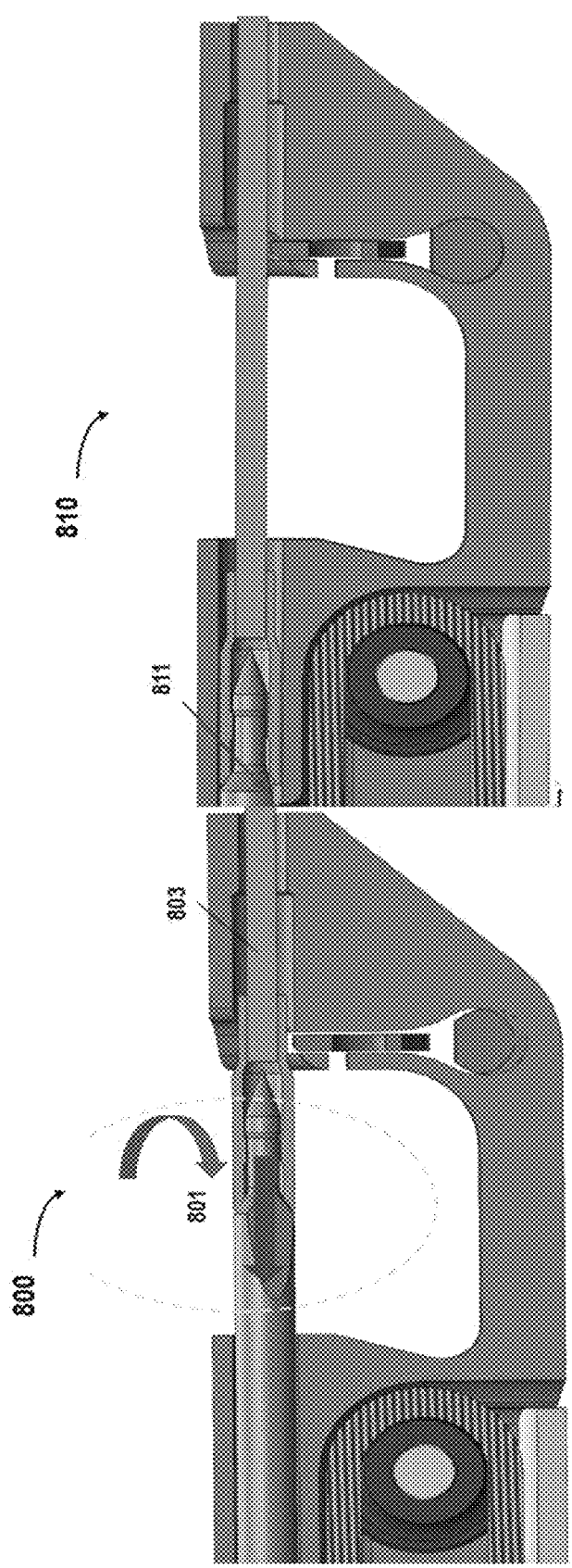

As described above, rotation of the needle into two different positions on alternating cycles (suture cycle and reset cycle) enables the ferrule to be docked and stripped. FIGS. 7-8 schematically shows a suturing cycle. At an initial state 700, a ferrule 701 is located in a pocket 702 at the distal end of the tissue aperture 704 in preparation for taking the next suturing bite. At the initial state, the ferrule 701 is detached from the needle 709. The ferrule may be secured in the pocket by a retention spring 703 capturing the ferrule proximal end (to prevent the ferrule from retracting) and a shoulder 705 capturing the ferrule taper (tapered surface 605 in FIG. 6 to prevent the ferrule from extending distally). It should be noted that the shoulder 705 may be formed at any location long the length (longitudinal axis direction) of the ferrule such as at the distal surface. The shoulder surface may or may not be tapered surface. In some cases, the shoulder surface may be parallel to the end surface of the ferrule. At the initial state the needle 709 may be orientated at an initial orientation where the facet or a flat surface 707 of the needle is rotated to a first side (e.g., right side) at a predetermined angle. The initial orientation may be a docking orientation.

Next, during the pierce and dock state 710, the needle 709 may extend or advance towards the distal end, piece tissue 711 captured in the tissue aperture. The tip of the needle may dock into the ferrule and be retained by a snap-in retention feature (e.g., bulb/wedge click) 713. The outer surface of the needle may compress the retention spring 703. During the extension state, the orientation of the needle may stay the same as the initial orientation i.e., docking orientation. The full length of the translational movement of the needle may be dependent on the width of the aperture 704 and/or length of a toggle plate as described later herein.

Subsequently, the needle may retract and draw suture 803 through tissue 801. The needle may retract along with the engaged ferrule with one end coupled to the suture 803. During the retraction state 800, the needle may be rotated towards a strip orientation while traversing back to the proximal end of the tissue aperture. The needle may be rotated in a direction such that the flat surface of the needle is rotated towards a strip orientation (e.g., downwards). Once the needle fully retracts to the proximal end 810, the needle may be oriented to a strip orientation. A user may operate the needle device to move it off of tissue in preparation for the reset cycle.

Figure 9:
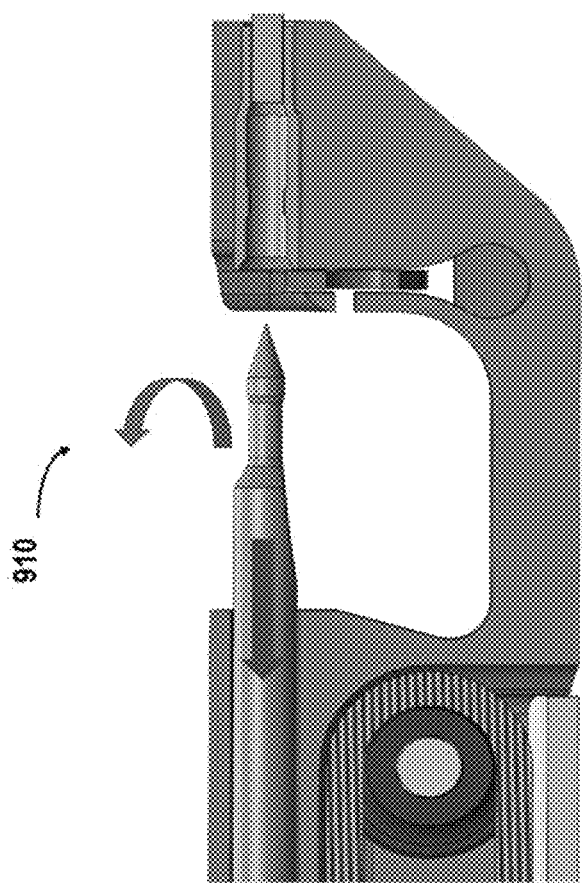
FIG. 9 schematically illustrates a reset cycle.
Figure 9:
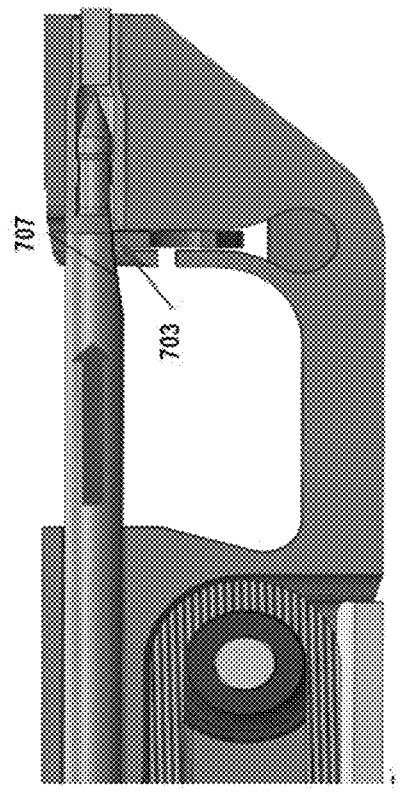

FIG. 9 schematically illustrates a reset cycle. During a reset cycle, the needle may extend or advance distally 900 to place the ferrule back to the pocket. The needle may maintain the strip orientation during the extension state 900 such that the flat surface 707 of the needle faces the retention spring 901. Once the ferrule is placed back to the pocket, the flat surface 707 allows the retention spring 703 to extend, trapping the ferrule. During the subsequent retraction state 910, the orientation of the needle may be rotated towards the docking orientation while traversing back to the proximal end of the tissue aperture. The needle may be rotated in an opposite direction such that the flat surface of the needle is rotated towards the docking orientation (e.g., right side) same as the initial state.

In some embodiments, the needle instrument may comprise a toggle-based rotation indexing mechanism. In some cases, the toggle-based rotation indexing mechanism may comprise a spring biased toggle and a channel plate to rotate the needle into either dock or strip index. The term dock/strip index may refer to the docking and stripping orientation which are utilized interchangeably throughout the specification.

Figure 2:
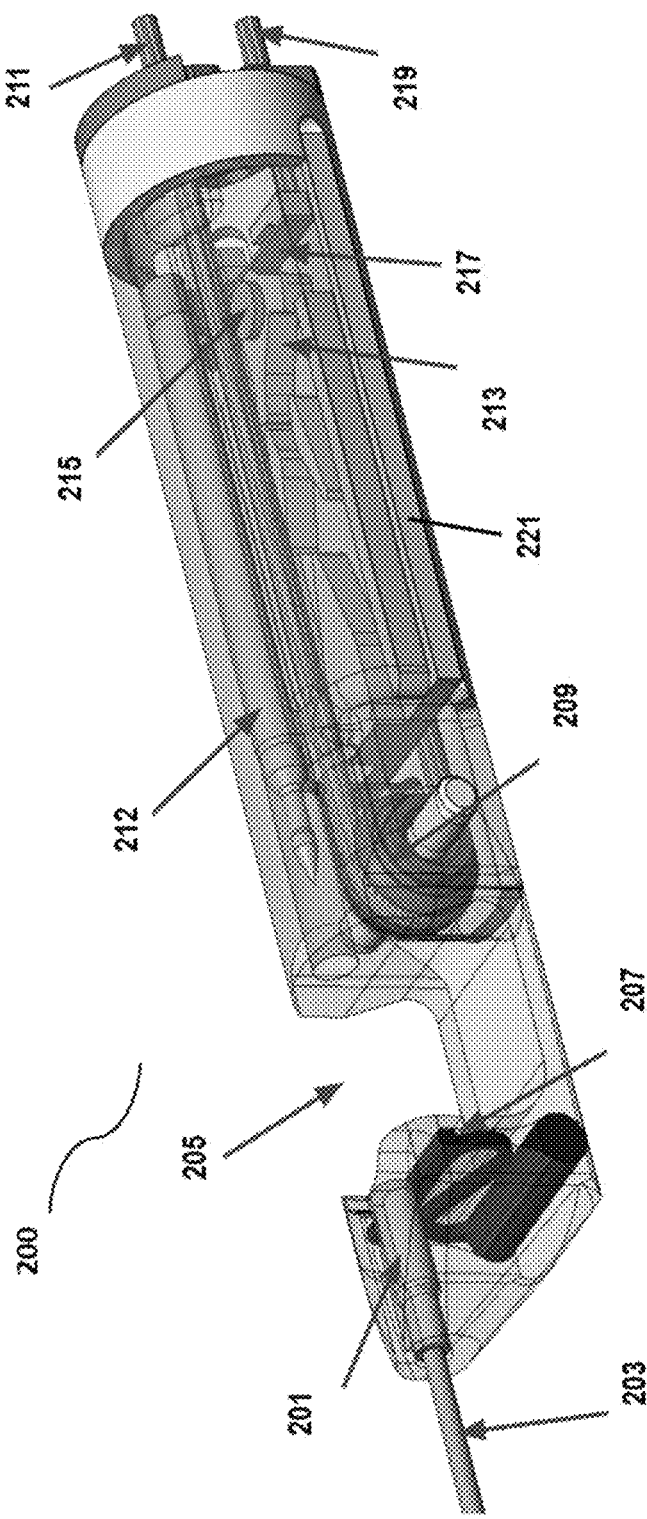
FIG. 2 shows an example of an end effector employing a toggle-based rotation indexing mechanism.

FIG. 2 shows an example of an end effector 200 employing the toggle-based rotation indexing mechanism. The end effector can be the same as the end effector 101 as described in FIG. 1. For instance, the end effector 200 may comprise a needle device and reside at the distal end of a flexible suturing instrument. The needle 212 may be driven forward and backward by antagonistic cables. The antagonistic cables herein may refer to the cables that pulling on one end of the cable advances the needle while pulling on the other end of the cable retracts the needle. For instance, the needle 212 may be driven forward by the needle insertion cable 219 to pass through the tissue aperture 205 (e.g., piercing the tissue) and then driven backward (e.g., drawing the suture through the resulting hole) by the needle retraction cable 211. The antagonistic cables may beneficially allow the end effector to be suitable for being used with a flexible articulating shaft. The needle driving mechanism may comprise a cable redirect pulley 209 to effectuate the translational movement of the needle. Such simple needle motion beneficially allows for reduced time and less dexterity which is suitable for robotic endoluminal platform. Details about the needle driving mechanism are described with respect to FIG. 3 and FIG. 4.

As described above, the needle may be driven forward to advance into a suture ferrule 201. The suture ferrule can be the same as the ferrule as described elsewhere herein. The suture ferrule 201 may be attached to suture 203 at a distal end. The suture ferrule 201 may be secured in the pocket at the distal end by a retention spring 207. The retention spring 207 can be the same as the retention spring as described in FIGS. 7-9.

Figure 6:
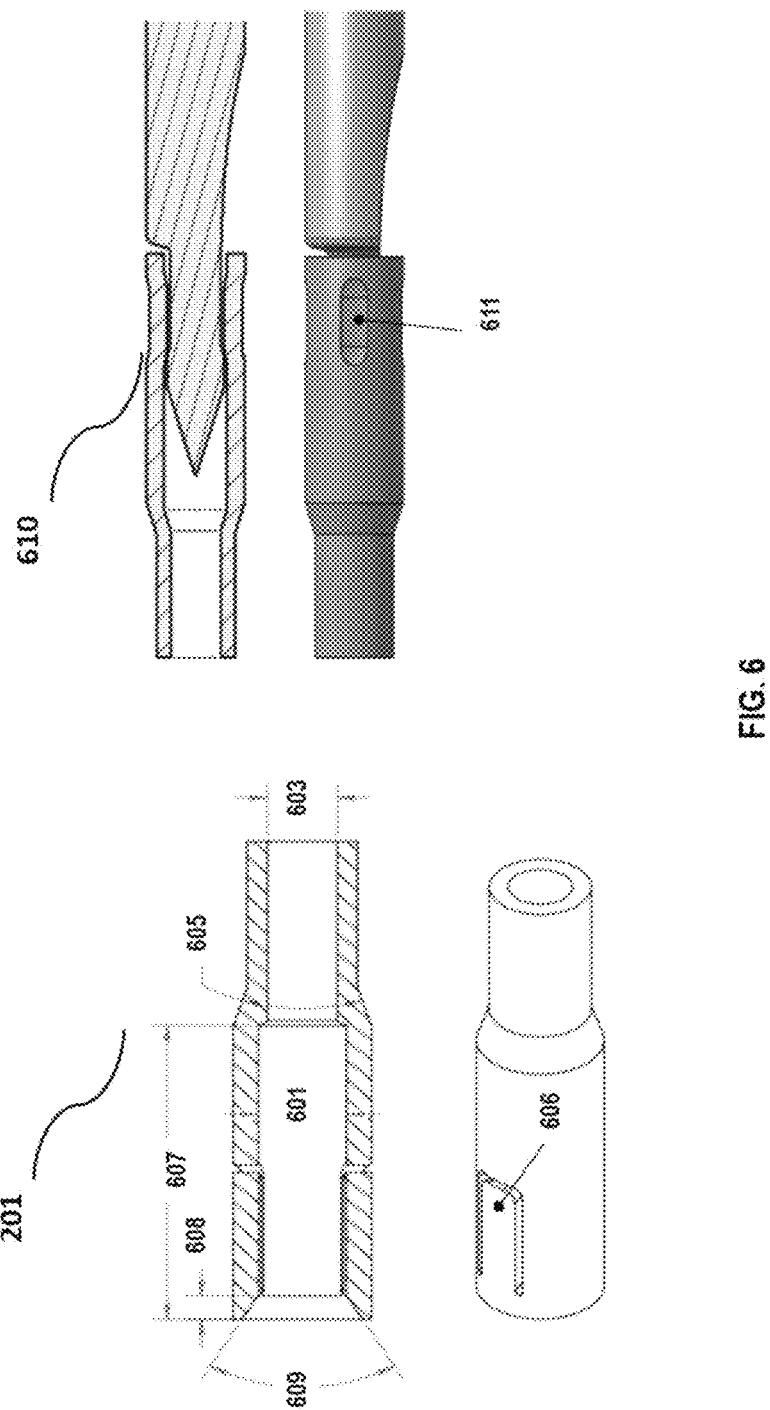
FIG. 6 shows an example of a ferrule.

FIG. 6 shows an example of a ferrule 201. In some embodiments, a ferrule 201 may comprise a substantially tubular body with a suture engaging aperture 603 and a needle engaging aperture 601. In some cases, the suture engaging aperture 603 may have a dimension (e.g., diameter) smaller than that of the needle engaging aperture 601. During manufacturing, a suture (e.g., suture 203) may be inserted into the suture aperture of the ferrule and swaged in place to couple the ferrule to the suture. In some cases, the suture aperture may have an exterior shape such as a tapered surface 605 to assist depositing the ferrule back to the end effector tip and to stop the ferrule from advancing further when it is deposited back to the pocket.

The needle engaging aperture 601 may comprise local wall deformations 611 or tabs 606 that can be deformed inwards to reduce the effective diameter of the needle engaging aperture. For example, the local wall deformation 611 may be crimp indentations. In some cases the tabs or local wall deformations may be integrally formed with the ferrule during manufacturing. Such deformations may allow the ferrule to couple to the needle 610 during operation of the device and prevent decoupling under forces supplied by tissue. The needle engaging aperture may have shaped inner surface with suitable dimensions and shape 608, 609 at the proximal opening to ease the docking with the needle tip. Such needle engaging aperture may also allow the needle to be sufficiently tapered for tissue dilation while ensuring the distance between the outer most ferrule and needle diameters is as small as possible to prevent ferrule disengagement during traversing.

The ferrule may be decoupled from the needle by the stripping feature in the distal end of the end effector, such that the ferrule is re-deposited back into the pocket in the end effector tip. The stripping feature may comprise the retention spring 207 in FIG. 2. Referring back to FIG. 2, the end effector may comprise a toggle-based rotation indexing mechanism. The indexing mechanism may comprise a toggle mechanism including toggle 213, a toggle spring 217, a toggle pivot 215, and a toggle plate 221 to switch the positions of the needle via a needle flag.

Figure 3:
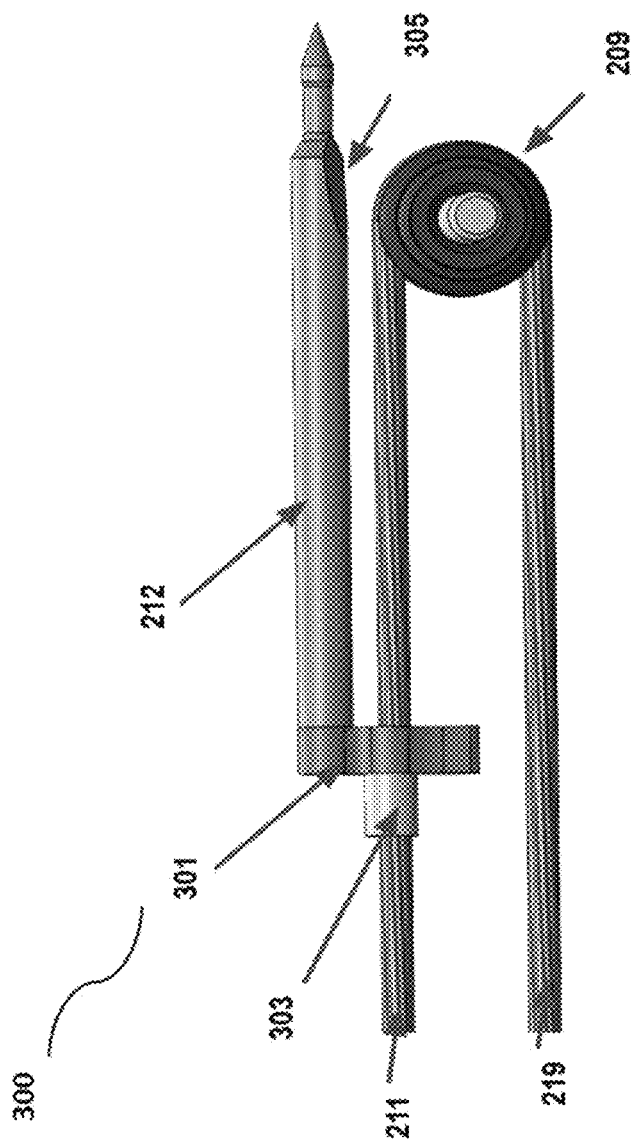
FIG. 3 an example of a needle drive mechanism.
Figure 4A:
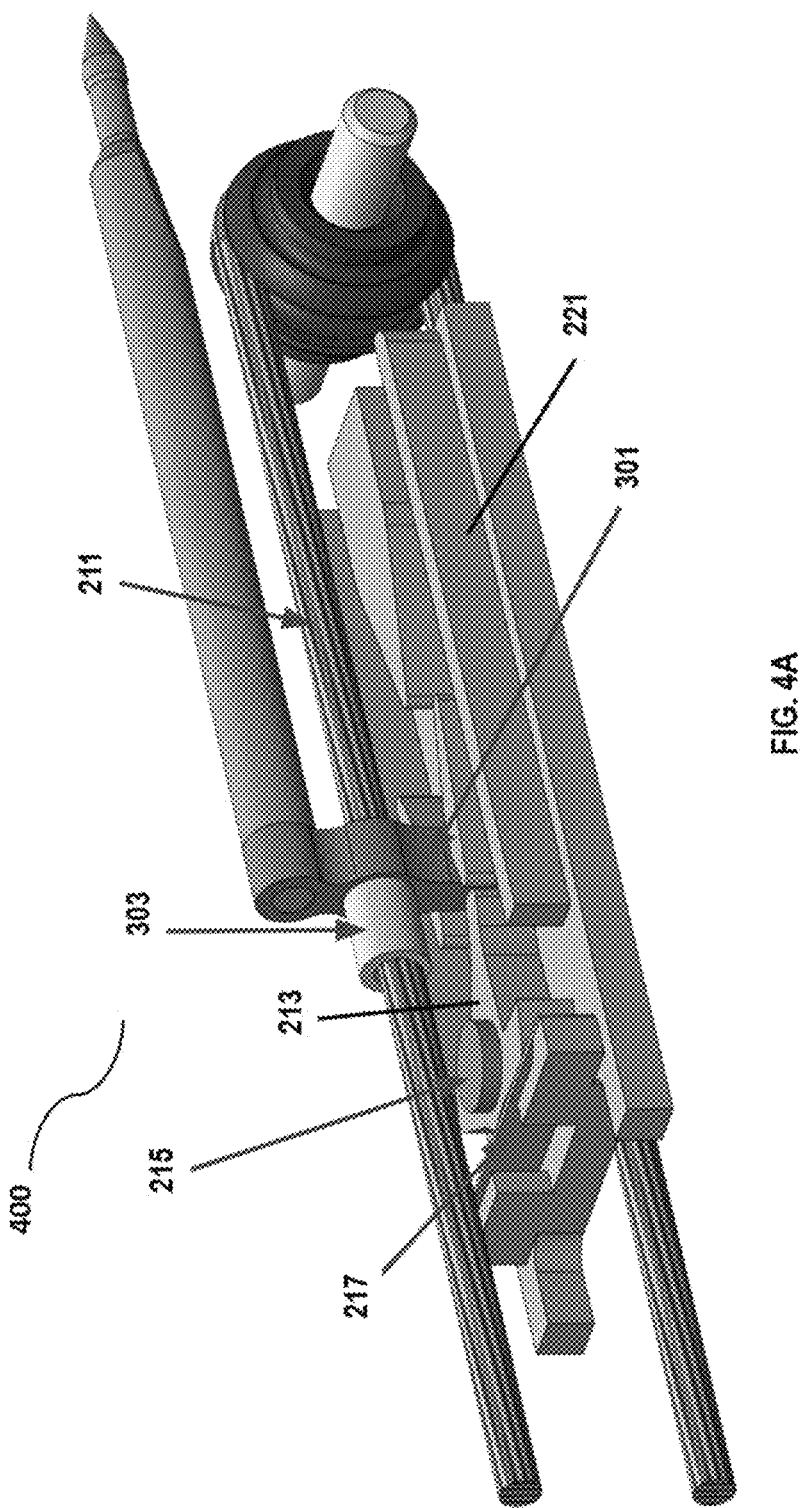
FIG. 4A and FIG. 4B shows an example of indexing mechanism.

FIG. 3 and FIG. 4A show an example of a needle drive mechanism 300 and an indexing mechanism 400. As shown in FIG. 3, the needle driving mechanism may comprise cables 211, 219 and a redirect pulley 209 to drive the needle moving forward and backward translationally. In some cases, the needle 212 may be attached to the needle retraction cable 211 via a needle flag 301 and cable crimp 303. The needle flag 301 may be fixedly attached to the needle such as by welded together or integrally formed by machining, MIM, over-molding or other manufacturing methods. The needle flag 301 may be fixedly coupled to the cable crimp 303 such as by being welded together. Such coupling mechanism beneficially allows for tension and deflection in the retraction cable 211 from the centerline thereby providing centering force biasing the needle rotation to a middle position. Alternatively, the needle flag may be directly coupled to the cable without the cable crimp.

Figure 4B:
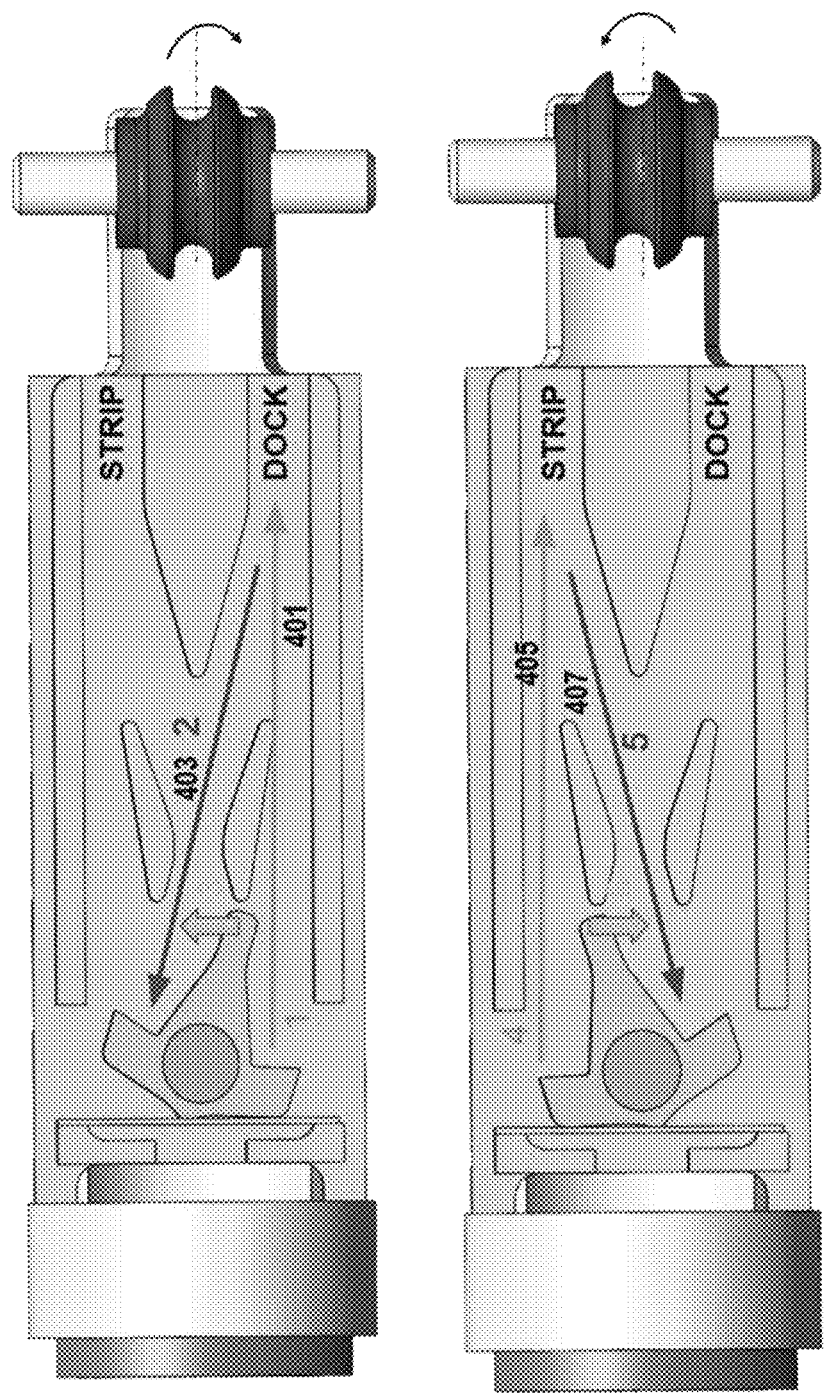

Rotation of the needle is controlled by the toggle 213 and toggle plate 221 interacting with the needle flag 301. As shown in FIG. 4A and FIG. 4B, as the needle extends (forward movement) and retracts (backward movement), a tail of needle flag 301 is placed in the track or channel in the toggle plate and follows different channels in the toggle plate 221 which rotate the needle into either the dock or strip orientations. The toggle plate 221 may have a substantially flat surface and the channels are formed on a substantially flat surface.

As illustrated in FIG. 4B, when the needle reaches the fully retracted position on each cycle (e.g., proximal end of the toggle plate), the needle flag 301 switches the position of the toggle, which rotates the needle to the opposite position for the subsequent cycle. The toggle 213 may be a bi-stable spring-loaded mechanism where the flat spring 217 proximal to the toggle may resist toggle rotation from one state to the other. When the needle flag 301 reaches the proximal end and presses against the toggle 213, the force from the needle flag, provided by the retraction cable, may act on the toggle to force it past the "over-center" resistance from the spring and into the other state (e.g., switch from the oblique channel 403/407 to either strip channel 405 or dock channel 401 that is parallel to the axial axis).

In the illustrated example, the toggle plate may include a plurality of channels. The plurality of channels may comprise a first channel for Strip and a second channel for Dock where orientation of the needle remains constant. The plurality of channels may further comprise a third channel for Toggle where needle orientation is oscillated between the Strip and Dock position. The toggle channel may include two entrances and two exits, where the exit is gated by the toggle, but the channel remains the same. For example, as shown in FIG. 4B, when the needle is at the initial state i.e., "position 1," (corresponds to initial state 700 as illustrated in FIG. 7), the toggle may be forced to the right side from the center state. Once the needle is driven forward (corresponding to pierce and dock state 710 as illustrated in FIG. 7), the tail of the needle flag moves along the first channel 401 towards the docking position (along the forward path or a substantially straight channel 401) and the orientation of the needle is maintained at the docking orientation while the needle flag is traveling along the first channel 401 (path 1). When the needle retracts back towards the proximal end (along path 2), the needle flag may follow along the toggle plate channel 403 (obliqued channel) in path 2 and reach the fully retracted position (position 4), the toggle may be forced to the opposite direction (e.g., left side) and the orientation of the needle is changed to the strip orientation while the needle travels along the second channel 403. When the needle advances in the reset cycle, the needle flag may travel along the toggle plate channel 405 (path 4) towards the strip position while maintaining the needle at the strip orientation. Once the needle retracts back (path 5) in the reset cycle, the needle flag may follow along the toggle plate channel 403 to retract back to the initial position.

In some cases, the back and forth rotation of the needle may be over an angle of about 60 degrees between the alternating cycles. Alternatively, the rotation range may be any number below 60 degrees or above 60 degrees. The range of rotation angle may be dependent on the dimension or shape of the flat surface of the needle to engage and disengage with the ferrule.

The unique toggle-based rotation mechanism may beneficially allow for a compact design and reduced size of the needle end effector. Traditional needle device may achieve orienting a needle facet utilizing a rotational cam. For instance, when the cam needle is fully retracted back and rotated 180° to orient an opposite side of shoulder towards a ferrule lath. However, such orientation changing is in one direction (clock-wise or counter-clockwise) in a continuous fashion and such cam mechanism can result in an increased diameter and length of the needle end effector. An increased dimension of a needle end effector may result in increased minimum curvature to maneuver inside a tortuous body passage. The toggle-based rotation mechanism of the present disclosure beneficially allows for a compact design of the needle end effector. The reduced dimension (e.g., diameter) of the end effector may allow for an improved anatomical access and may permit use in conjunction with additional tissue manipulation instruments (e.g., graspers) for tissue placement and suture management. Additionally, an endoluminal device with the provided end effector may have an overall reduced diameter allowing for higher quality and more rapid lesion closure than existing technologies when used in conjunction with a robotic surgical platform.

Figure 5A:
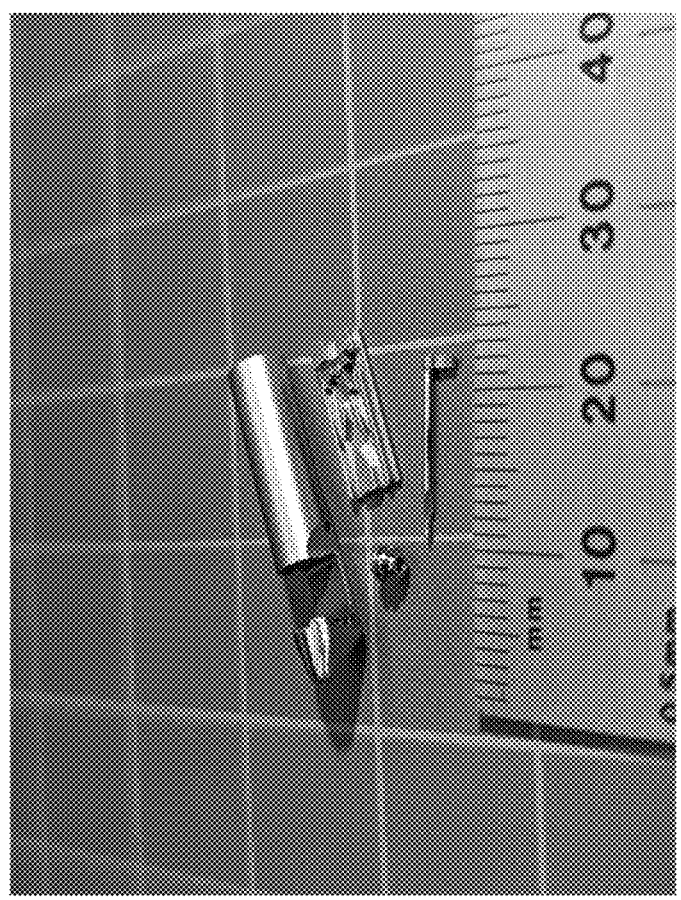

FIG. 5A and FIG. 5B shows example of dimension of a needle end effector. For example, the outer diameter 511 of the instrument may be no greater than 5 millimeters (mm), 4.9 mm, 4.8 mm, 4.7 mm, 4.6 mm, 4.5 mm, 4.4 mm, 4.3 mm, 4.2 mm, 4.1 mm, 4 mm, 3.5 mm, 3 mm, any number in between the above numbers or any number greater than 5 mm or small than 3 mm. The total length 501 of the needle end effector may be no greater than 30 mm, 29 mm, 28 mm, 27 mm, 26 mm, 25 mm, 24 mm, 23 mm, 22 mm, 21 mm, 20 mm, 19 mm, 18 mm, 17 mm, 16 mm, 15 mm, any number in between the above numbers or any number greater than 30 mm or small than 15 mm. In some cases, the overall size of the needle end effector e.g., total length and diameter may be substantially dependent on the tissue aperture size (e.g., tissue aperture length 502 and depth 503). The length 504 of the end effector tip may be substantially dependent on the ferrule length (e.g., sum of length of the needle aperture portion 607 and the suture aperture portion).

The toggle mechanism 500 may comprise a toggle 213, a toggle spring 217, a toggle pivot 215, and a toggle plate 221. As described above, the toggle mechanism may switch the positions of the needle by interacting with a needle flag. The toggle mechanism 500 may be substantially a planar plate formed with slots to engage with the needle flag. The slots are formed on a substantially flat surface of the planar plate. The slots may guide the needle flag to various angles when the needle flag follows different paths. The different paths may be formed by a slot that is obliquely oriented with respect to the axial axis (i.e., length direction) and a slot that is substantially parallel to the axial axis. In some cases, the different paths may comprise a path substantially parallel to the axial axis when the needle is driven forward and an obliquely oriented path when the needle is driven backward.

As shown in the example, the slots may have a dimension that permits smooth traversing of the needle flag. In some cases, the width of the slot may vary at different locations considering the needle flag is orientated at different angles along the slot. For example, the width 516 may be smaller than the width 515, width 519 or width 517. The obliquely oriented slot may be formed by angled island features 512, 513, 514, 518 to guide the needle flag into different paths. The toggle may have a shape that permits it to rotate to an off-centered angle 512. As described above, the toggle-based rotation mechanism permits the needle to be rotated back and forth over a pre-determined angle range such as a range about 60 degrees between the alternating cycles. Alternatively, the rotation range may be any number below 60 degrees or above 60 degrees.

The toggle mechanism can be formed of any suitable material. For example, the toggle plate, toggle and the like may be formed of stainless steel, or other rigid material. Forming tracks or slots on a substantially planar surface may allow for an easy manufacturing process thereby lowering the cost.

Flexible Endoscope

Figure 10:
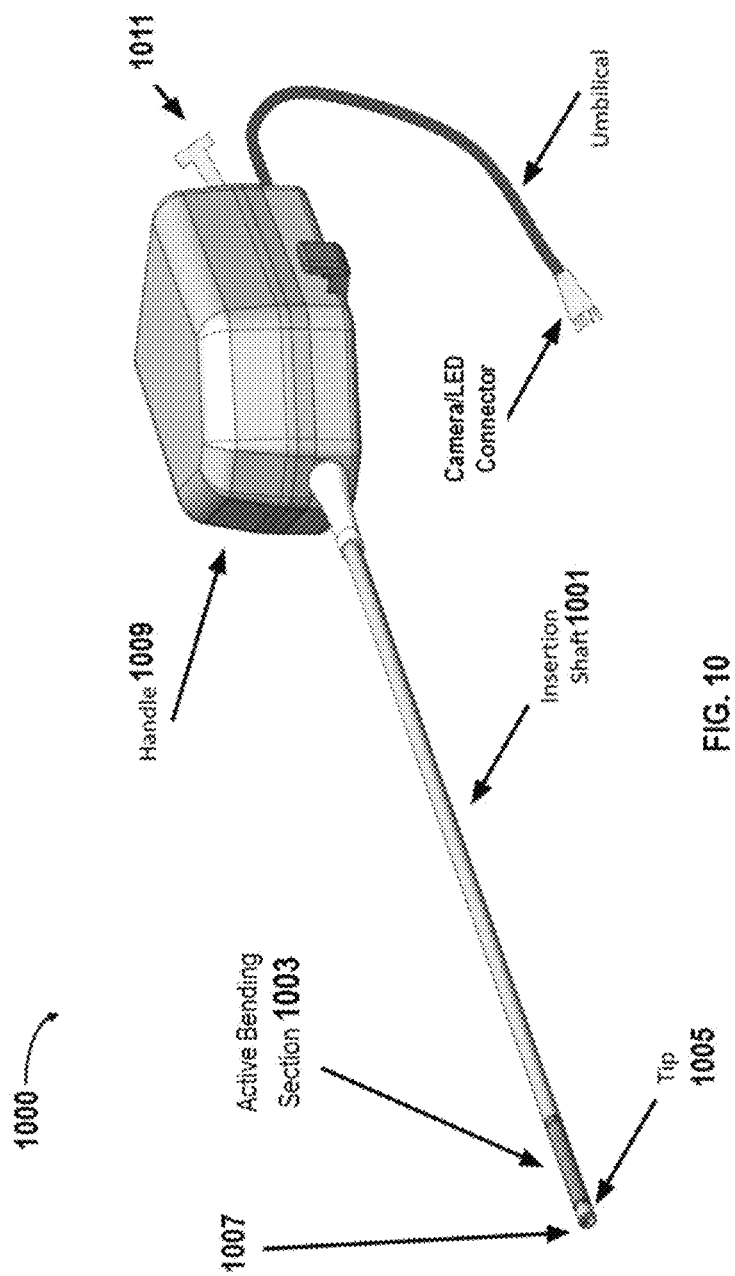
FIG. 10 illustrates an example of a flexible endoscope.

The provided suturing instrument may be utilized by any robotic endoluminal systems or platforms. In an aspect of the invention, the suturing instrument may be inserted through a working channel of a flexible endoscope to perform suturing operations as described above. The suturing instrument may be independently steerable from the endoscope. For example, the suturing instrument shaft may be advanced and retracted and rotated relative to the flexible endoscope. FIG. 10 illustrates an example of a flexible endoscope 1000, in accordance with some embodiments of the present disclosure. As shown in FIG. 10, the flexible endoscope 1000 may comprise a handle/proximal portion 1009 and a flexible elongate member to be inserted inside of a subject. The flexible elongate member can be the same as the one described above. In some embodiments, the flexible elongate member may comprise a proximal shaft (e.g., insertion shaft 1001), steerable tip (e.g., tip 1005), a steerable section (active bending section 1003) and a proximal shaft section 100. The endoscope 1000 may also be referred to as steerable catheter assembly as described elsewhere herein. In some cases, the endoscope 1000 may be a single-use robotic endoscope. In some cases, the entire catheter assembly may be disposable. In some cases, at least a portion of the catheter assembly may be disposable. In some cases, the entire endoscope may be released from an instrument driving mechanism and can be disposed of. In some embodiments, the endoscope may contain varying levels of stiffness along the shaft, as to improve functional operation.

The endoscope or steerable catheter assembly 1000 may comprise a handle portion 1009 that may include one or more components configured to process image data, provide power, or establish communication with other external devices. For instance, the handle portion may include a circuitry and communication elements that enables electrical communication between the steerable catheter assembly 1000 and an instrument driving mechanism (not shown), and any other external system or devices. In another example, the handle portion 1009 may comprise circuitry elements such as power sources for powering the electronics (e.g., camera, electromagnetic sensor and LED lights) of the endoscope.

The one or more components located at the handle may be optimized such that expensive and complicated components may be allocated to the robotic support system, a hand-held controller or an instrument driving mechanism thereby reducing the cost and simplifying the design of the disposable endoscope. The handle portion or proximal portion may provide an electrical and mechanical interface to allow for electrical communication and mechanical communication with the instrument driving mechanism. The instrument driving mechanism may comprise a set of motors that are actuated to rotationally drive a set of pull wires of the catheter. The handle portion of the catheter assembly may be mounted onto the instrument drive mechanism so that its pulley/capstans assemblies are driven by the set of motors. The number of pulleys may vary based on the pull wire configurations. In some cases, one, two, three, four, or more pull wires may be utilized for articulating the flexible endoscope or catheter.

The handle portion may be designed allowing the robotic endoscope to be disposable at reduced cost. For instance, classic manual and robotic endoscopes may have a cable in the proximal end of the endoscope handle. The cable often includes illumination fibers, camera video cable, and other sensors fibers or cables such as electromagnetic (EM) sensors, or shape sensing fibers. Such complex cable can be expensive adding to the cost of the endoscope. The provided robotic endoscope may have an optimized design such that simplified structures and components can be employed while preserving the mechanical and electrical functionalities. In some cases, the handle portion of the robotic endoscope may employ a cable-free design while providing a mechanical/electrical interface to the catheter.

The electrical interface (e.g., printed circuit board) may allow image/video data and/or sensor data to be received by the communication module of the instrument driving mechanism and may be transmitted to other external devices/systems. In some cases, the electrical interface may establish electrical communication without cables or wires. For example, the interface may comprise pins soldered onto an electronics board such as a printed circuit board (PCB). For instance, a receptacle connector (e.g., the female connector) is provided on the instrument driving mechanism as the mating interface. This may beneficially allow the endoscope to be quickly plugged into the instrument driving mechanism or robotic support without utilizing extra cables. Such type of electrical interface may also serve as a mechanical interface such that when the handle portion is plugged into the instrument driving mechanism, both mechanical and electrical coupling is established. Alternatively or in addition to, the instrument driving mechanism may provide a mechanical interface only. The handle portion may be in electrical communication with a modular wireless communication device or any other user device (e.g., portable/hand-held device or controller) for transmitting sensor data and/or receiving control signals.

In some cases, the handle portion 1009 may comprise one or more mechanical control modules such as lure 1011 for interfacing the irrigation system/aspiration system. In some cases, the handle portion may include a lever/knob for articulation control. Alternatively, the articulation control may be located at a separate controller attached to the handle portion via the instrument driving mechanism.

The endoscope may be attached to a robotic support system or a hand-held controller via the instrument driving mechanism. The instrument driving mechanism may be provided by any suitable controller device (e.g., hand-held controller) that may or may not include a robotic system. The instrument driving mechanism may provide mechanical and electrical interface to the steerable catheter assembly 1000. The mechanical interface may allow the steerable catheter assembly 1000 to be releasably coupled to the instrument driving mechanism. For instance, the handle portion of the steerable catheter assembly can be attached to the instrument driving mechanism via quick install/release means, such as magnets, spring-loaded levers and the like. In some cases, the steerable catheter assembly may be coupled to or released from the instrument driving mechanism manually without using a tool. Details about the instrument driving mechanism are described later herein.

In the illustrated example, the distal tip of the catheter or endoscope shaft is configured to be articulated/bent in two or more degrees of freedom to provide a desired camera view or control the direction of the endoscope. As illustrated in the example, imaging device (e.g., camera), position sensors (e.g., electromagnetic sensor) 1007 is located at the tip of the catheter or endoscope shaft 1005. For example, line of sight of the camera may be controlled by controlling the articulation of the active bending section 1003. In some instances, the angle of the camera may be adjustable such that the line of sight can be adjusted without or in addition to articulating the distal tip of the catheter or endoscope shaft. For example, the camera may be oriented at an angle (e.g., tilt) with respect to the axial direction of the tip of the endoscope with the aid of an optical component.

The distal tip 1005 may be a rigid component that allows for positioning sensors such as imaging devices (e.g., camera) and other electronic components (e.g., LED light source) being embedded at the distal tip. Depending on the type of the endoscope, the distal tip may comprise other sensors such as electromagnetic (EM) sensors or inertial measurement units.

The robotic endoscope may or may not have real-time EM tracking capability. In the case that the robotic endoscope is embedded with EM sensor, the EM sensor comprising of one or more sensor coils embedded in one or more locations and orientations in the medical instrument (e.g., tip of the endoscopic tool) measures the variation in the EM field created by one or more static EM field generators positioned at a location close to a patient. The location information detected by the EM sensors is stored as EM data. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. For example, the EM field generator may be positioned close to the patient during a procedure to locate the EM sensor position in 3D space or may locate the EM sensor position and orientation in 5D or 6D space. This may provide a visual guide to an operator when driving the endoscope towards the target site.

The endoscope may have a unique design in the elongate member. In some cases, the active bending section 1003 and the proximal shaft 1001 of the endoscope may consist of a single tube that incorporates a series of cuts (e.g., reliefs, slits, etc.) along its length to allow for improved flexibility, a desirable stiffness as well as the anti-prolapse feature (e.g., features to define a minimum bend radius).

As described above, the active bending section 1003 may be designed to allow for bending in two or more degrees of freedom (e.g., articulation). A greater bending degree such as 180 and 270 degrees (or other articulation parameters for clinical indications) can be achieved by the unique structure of the active bending section. In some cases, the active bending section and/or the passive section may be fabricated separately as a modular component and assembled to the proximal shaft. In some cases, the cut patterns of the active bending and passive sections may be different such that at least the minimum bend radius of the two sections may be different. In some cases, a variable minimum bend radius along the axial axis of the elongate member may be provided such that an active bending section or the passive section may comprise two or more different minimum bend radii.

The articulation of the endoscope may be controlled by applying force to the distal end of the endoscope via one or multiple pull wires. The one or more pull wires may be attached to the distal end of the endoscope. In the case of multiple pull wires, pulling one wire at a time may change the orientation of the distal tip to pitch up, down, left, right or any direction needed. In some cases, the pull wires may be anchored at the distal tip of the endoscope, running through the bending section, and entering the handle where they are coupled to a driving component (e.g., pulley). This handle pulley may interact with an output shaft from the robotic system.

In some embodiments, the proximal end or portion of one or more pull wires may be operatively coupled to various mechanisms (e.g., gears, pulleys, capstans, etc.) in the handle portion of the catheter assembly. The pull wire may be a metallic wire, cable or thread, or it may be a polymeric wire, cable or thread. The pull wire can also be made of natural or organic materials or fibers. The pull wire can be any type of suitable wire, cable or thread capable of supporting various kinds of loads without deformation, significant deformation, or breakage. The distal end/portion of one or more pull wires may be anchored or integrated to the distal portion of the catheter, such that operation of the pull wires by the control unit may apply force or tension to the distal portion which may steer or articulate (e.g., up, down, pitch, yaw, or any direction in-between) at least the distal portion (e.g., flexible section) of the catheter.

The pull wires may be made of any suitable material such as stainless steel (e.g., SS316), metals, alloys, polymers, nylons or biocompatible material. Pull wires may be a wire, cable or a thread. In some embodiments, different pull wires may be made of different materials for varying the load bearing capabilities of the pull wires. In some embodiments, different sections of the pull wires may be made of different material to vary the stiffness and/or load bearing along the pull. In some embodiments, pull wires may be utilized for the transfer of electrical signals.

The proximal design may improve the reliability of the device without introducing extra cost allowing for a low-cost single-use endoscope. In another aspect of the invention, a single-use robotic endoscope is provided. The robotic endoscope may be a gastroscope and can be the same as the steerable catheter assembly as described elsewhere herein. Traditional endoscopes can be complex in design and are usually designed to be re-used after procedures, which require thorough cleaning, dis-infection, or sterilization after each procedure. The existing endoscopes are often designed with complex structures to ensure the endoscopes can endure the cleaning, dis-infection, and sterilization processes. The provided robotic endoscope can be a single-use endoscope that may beneficially reduce cross-contamination between patients and infections. In some cases, the robotic gastroscope may be delivered to the medical practitioner in a pre-sterilized package and are intended to be disposed of after a single use.

Figure 11:
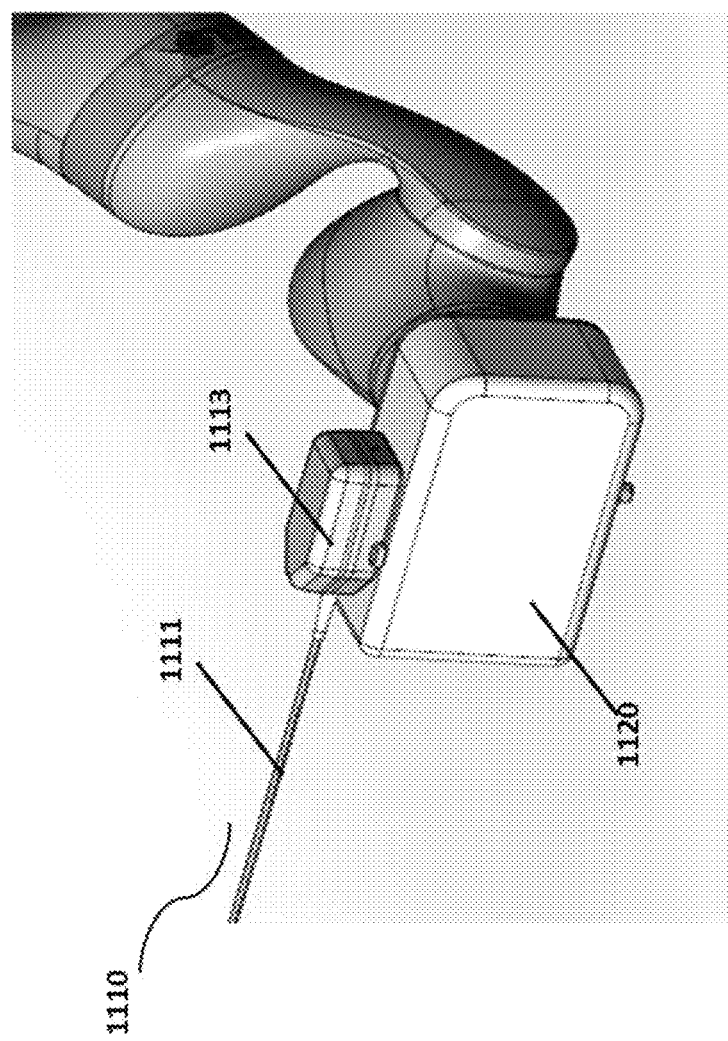
FIG. 11 shows an example of a robotic endoscope (e.g., gastroscope or colonoscope).

As shown in FIG. 11, a robotic endoscope (e.g., gastroscope or colonoscope) 1110 may comprise a handle portion 1113 and a flexible elongate member 1111. In some embodiments, the flexible elongate member 1111 may comprise a shaft, steerable tip, a steerable/active bending section and optionally an anti-prolapse passive section. The robotic gastroscope 1110 can be the same as the steerable catheter assembly as described in FIG. 10. The robotic gastroscope may be a single-use robotic endoscope. In some cases, only the catheter may be disposable. In some cases, at least a portion of the catheter may be disposable. In some cases, the entire robotic gastroscope may be released from the instrument driving mechanism and can be disposed of. In some cases, the gastroscope may contain varying levels of stiffness along its shaft, as to improve functional operation. In some cases, a minimum bend radius along the shaft may vary so that the kink resistance or anti-prolapse capability may be configurable along the length.

The robotic gastroscope can be releasably coupled to an instrument driving mechanism 1120. The instrument driving mechanism 1120 may be mounted to the arm of the robotic support system or to any actuated support system as described elsewhere herein. The instrument driving mechanism may provide mechanical and electrical interface to the robotic gastroscope 1110. The mechanical interface may allow the robotic gastroscope 1110 to be releasably coupled to the instrument driving mechanism. For instance, the handle portion of the robotic gastroscope can be attached to the instrument driving mechanism via quick install/release means, such as magnets and spring-loaded levels. In some cases, the robotic gastroscope may be coupled or released from the instrument driving mechanism manually without using a tool.

FIG. 12A and FIG. 12B shows an example of an instrument driving mechanism (IDM) 1220 providing a mechanical interface to the handle portion of the robotic endoscope. In some cases, the IDM 1220 for a robotic endoscope and one or more IDMs for one or more instruments (e.g., suturing instrument) 1231, 1233 may be attached to the robotic arm 1200. As shown in the example, the instrument driving mechanism (IDM) 1220 for the robotic endoscope may comprise a set of motors 1221 that are actuated to rotationally drive a set of pull wires of the flexible endoscope or catheter. The handle portion of the catheter assembly may be mounted onto the instrument drive mechanism 1220 so that its pulley assemblies or capstans are driven by the set of motors. The number of pulleys may vary based on the pull wire configurations. In some cases, one, two, three, four, or more pull wires may be utilized for articulating the flexible endoscope or catheter. Similarly, the instrument driving mechanism (IDM) 1231 for the suturing instrument herein may comprise a set of motors 1235 that are actuated to rotationally drive a set of pull wires of the suturing instrument thereby controlling the articulation of the bending sections of the suturing instrument, the roll movement and suture operation of the needle end effector as described above.

The handle portion may be designed allowing the robotic gastroscope to be disposable at reduced cost. For instance, classic manual and robotic gastroscopes may have a cable in the proximal end of the gastroscope handle. The cable often includes illumination fibers, camera video cable, and other optional sensor fibers or cables such as electromagnetic (EM) sensors, or shape sensing fibers. Such complex cable can be expensive, adding to the cost of the gastroscope. The provided robotic gastroscope may have an optimized design such that simplified structures and components can be employed while preserving the mechanical and electrical functionalities. In some cases, the handle portion of the robotic gastroscope may employ a cable-free design while providing a mechanical/electrical interface to the catheter.

Figure 13:
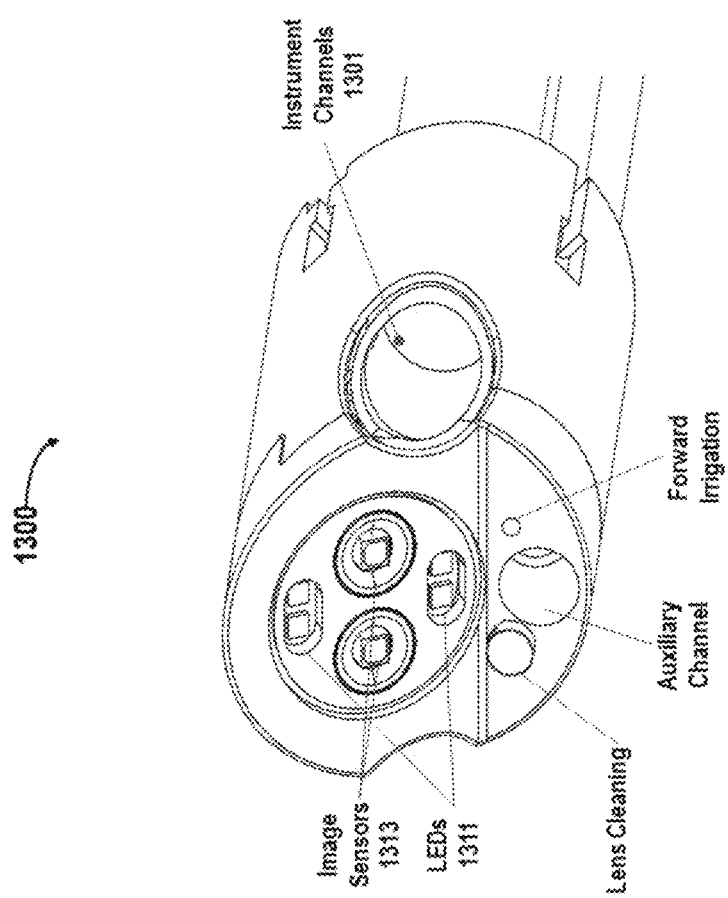
FIG. 13 shows an example of a distal tip of an endoscope.

FIG. 13 shows an example of a distal tip 1300 of an endoscope. In some cases, the distal portion or tip of the endoscope 1300 may be substantially flexible such that it can be steered into one or more directions (e.g., pitch, yaw). The endoscope may comprise a tip portion, bending section, and insertion shaft. In some embodiments, the endoscope may have variable bending stiffness along the longitudinal axis direction. For instance, the endoscope may comprise multiple sections having different bending stiffness (e.g., flexible, semi-rigid, and rigid). The bending stiffness may be varied by selecting materials with different stiffness/rigidity, varying structures in different segments (e.g., cuts, patterns), adding additional supporting components or any combination of the above. In some embodiments, the endoscope may have variable minimum bend radius along the longitudinal axis direction. The selection of different minimum bend radius at different locations along the endoscope may beneficially provide anti-prolapse capability while still allowing the endoscope to reach hard-to-reach regions. In some cases, a proximal end of the endoscope needs not be bent to a high degree thus the proximal portion of the endoscope may be reinforced with additional mechanical structure (e.g., additional layers of materials) to achieve a greater bending stiffness. Such a design may provide support and stability to the endoscope. In some cases, the variable bending stiffness may be achieved by using different materials during extrusion of the endoscope. This may advantageously allow for different stiffness levels along the shaft of the endoscope in an extrusion manufacturing process without additional fastening or assembling of different materials.

The distal portion of the endoscope may be steered by one or more pull wires. The distal portion of the endoscope may be made of any suitable material such as co-polymers, polymers, metals or alloys such that it can be bent by the pull wires. In some embodiments, the proximal end or terminal end of one or more pull wires may be coupled to a driving mechanism (e.g., gears, pulleys, capstan etc.) via the anchoring mechanism as described above. The distal end or portion of one or more pull wires may be anchored or integrated to the distal portion of the endoscope, such that operation of the pull wires by the control unit may apply force or tension to the distal portion which may steer or articulate (e.g., up, down, pitch, yaw, or any direction in-between) at least the distal portion (e.g., flexible section) of the endoscope.

The endoscope may have a dimension so that one or more electronic components can be integrated to the endoscope. For example, the outer diameter of the distal tip may range from 3 mm to 25 mm, and the diameter of the instrument channels 1301 may range from 2 mm to 6 mm such that one or more instruments can be removably inserted through the endoscope to the surgical site. However, it should be noted that based on different applications, the outer diameter can be in any range smaller than 3 mm or greater than 25 mm, and the diameter of the instrument channels 1301 can be in any range such as about 4 mm or 5 mm to allow the suturing instrument herein passing through. The space not occupied by fluidics or instrument pass throughs can be used to embed electronic components into the wall of the endoscope.

The one or more electronic components may comprise an imaging device, illumination device or other optional sensors. In some embodiments, the imaging device may be a video camera 1313. The imaging device may comprise optical elements and image sensor for capturing image data. The image sensors may be configured to generate image data in response to wavelengths of light. A variety of image sensors may be employed for capturing image data such as complementary metal oxide semiconductor (CMOS) or charge-coupled device (CCD). The imaging device may be a low-cost camera. In some cases, the image sensor may be provided on a circuit board. The circuit board may be an imaging printed circuit board (PCB). The PCB may comprise a plurality of electronic elements for processing the image signal. For instance, the circuit for a CCD sensor may comprise A/D converters and amplifiers to amplify and convert the analog signal provided by the CCD sensor. Optionally, the image sensor may be integrated with amplifiers and converters to convert analog signal to digital signal such that a circuit board may not be required. In some cases, the output of the image sensor or the circuit board may be image data (digital signals) can be further processed by a camera circuit or processors of the camera. In some cases, the image sensor may comprise an array of optical sensors.

The illumination device may comprise one or more light sources 1311 positioned at the distal tip. The light source may be a light-emitting diode (LED), an organic LED (OLED), a quantum dot, or any other suitable light source. In some cases, the light source may be a miniaturized LED for a compact design or Dual Tone Flash LED Lighting.

The imaging device and the illumination device may be integrated to the endoscope. For example, the distal portion of the endoscope may comprise suitable structures matching at least a dimension of the imaging device and the illumination device. The imaging device and the illumination device may be embedded into the catheter. A camera may be located at the distal portion 1300. The distal tip may have a structure to receive the camera, and illumination device. For example, the camera may be embedded into a cavity at the distal tip of the catheter. The cavity 1410 may be integrally formed with the distal portion of the cavity and may have a dimension matching a length/width of the camera such that the camera may not move relative to the endoscope. The camera may be adjacent to one or more instrument channels 1301 of the endoscope to provide near field view of the tissue or the organs. In some cases, the attitude or orientation of the imaging device may be controlled by controlling a rotational movement (e.g., roll) of the endoscope.

The power to the camera may be provided by a wired cable. In some cases, the cable wire may be in a wire bundle providing power to the camera as well as illumination elements or other circuitry at the distal tip of the endoscope. The camera and/or light source may be supplied with power from a power source located at the handle portion via wires, copper wires, or via any other suitable means running through the length of the catheter. In some cases, real-time images or video of the tissue or organ may be transmitted to an external user interface or display wirelessly. The wireless communication may be WiFi, Bluetooth, RF communication or other forms of communication. In some cases, images or videos captured by the camera may be broadcasted to a plurality of devices or systems. In some cases, image and/or video data from the camera may be transmitted down the length of the catheter to the processors situated in the handle portion via wires, copper wires, or via any other suitable means. The image or video data may be transmitted via the wireless communication component in the handle portion to an external device/system. In some cases, the system may be designed such that no wires are visible or exposed to operators.

In conventional endoscopy, illumination light may be provided by fiber cables that transfer the light of a light source located at the proximal end of the endoscope, to the distal end of the robotic endoscope. In some embodiments of the disclosure, miniaturized LED lights may be employed and embedded into the distal portion of the catheter to reduce the design complexity. In some cases, the distal portion may comprise a structure having a dimension matching a dimension of the miniaturized LED light source. As shown in the illustrated example, two cavities may be integrally formed with the endoscope to receive two LED light sources 1311. For instance, the outer diameter of the distal tip may range from 3 mm to 25 mm and diameter of the working channel of the endoscope may be around 4.5 or 6 mm such that two LED light sources may be embedded at the distal end. The outer diameter can be in any range smaller than 3 mm or greater than 25 mm, and the diameter of the instrument channels 1301 can be in any range according to the tool's dimensional or specific application. Any number of light sources may be included. The internal structure of the distal portion may be designed to fit any number of light sources.

In some cases, each of the LEDs may be connected to power wires which may run to the proximal handle. In some embodiments, the LEDs may be soldered to separated power wires that later bundle together to form a single strand. In some embodiments, the LEDs may be soldered to pull wires that supply power. In other embodiments, the LEDs may be crimped or connected directly to a single pair of power wires. In some cases, a protection layer such as a thin layer of biocompatible glue may be applied to the front surface of the LEDs to provide protection while allowing light emitted out. In some cases, an additional cover may be placed at the forwarding end face of the distal tip providing precise positioning of the LEDs as well as sufficient room for the glue. The cover may be composed of transparent material matching the refractive index of the glue so that the illumination light may not be obstructed.

The working channel (e.g., instrument channel 1301, auxiliary channel) may be designed to provide protection for the internal components such as flexible instruments (e.g., suturing instrument, forceps, etc.). When flexible instruments pass through a conventional working channel, they may be obstructed by the working channel due to kinking, ovalizing and/or high friction force. The working channel may provide a high hoop strength and a capability of achieving low bend radius. The working channel may also be designed to provide low friction in the inner surface. The suturing instrument as described herein may be passed through the working channel and advanced over the distal tip of the endoscope or retracted back into the working channel.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A suturing instrument comprising:
   a flexible shaft comprising an articulatable bending section, wherein the articulable bending section is actuated by one or more pull wires and a proximal end of the one or more pull wires are coupled to a handle of the suturing instrument; and
   a needle end effector located at a distal end of the articulatable bending section, wherein rotation mechanism is located at the needle end effector to switch an orientation of a needle about an axial axis of the needle to engage and disengage the needle with a ferrule, wherein the rotation mechanism comprises a substantially planar plate and one or more channels.

2. The suturing instrument of claim 1, wherein the needle is rotated back and forth over a predetermined range of angles with respect to the axial axis of the needle to switch the orientation.

3. The suturing instrument of claim 2, wherein the predetermined range of angles is about 60°.

4. The suturing instrument of claim 1, wherein the one or more channels are formed on a substantially flat surface of the substantially planar plate.

5. The suturing instrument of claim 1, wherein the rotation mechanism comprises a spring biased toggle to switch the needle from a channel oblique to an axial axis of the needle end effector to a channel parallel to the axial axis of the needle end effector.

6. The suturing instrument of claim 1, wherein the rotation mechanism comprises a cable to drive a forward and backward motion of the needle.

7. The suturing instrument of claim 6, wherein a proximal end of the cable is coupled to the handle.

8. The suturing instrument of claim 7, wherein the cable is an antagonistic cable and the proximal end of the cable is coupled to a pulley located at the handle.

9. The suturing instrument of claim 1, wherein a length of the needle end effector is not greater than 30 mm.

10. The suturing instrument of claim 1, wherein a diameter of the needle end effector is not greater than 5 mm.

11. The suturing instrument of claim 1, wherein the needle end effector is rotatable relative to the articulatable bending section.

12. The suturing instrument of claim 1, wherein the needle end effector is fixedly coupled to the articulatable bending section.

13. The suturing instrument of claim 1, wherein the handle is releasably coupled to a robotic support via a first instrument driving mechanism.

14. The suturing instrument of claim 13, wherein the first instrument driving mechanism drives an articulation motion of the articulable bending section and an operation of the needle end effector.

15. The suturing instrument of claim 1, wherein the suturing instrument is inserted through a working channel of a flexible robotic endoscope.

16. The suturing instrument of claim 15, wherein the flexible robotic endoscope comprises an articulable bending section.

17. The suturing instrument of claim 16, wherein the flexible robotic endoscope is releasably coupled to a robotic support via a second instrument driving mechanism.

18. The suturing instrument of claim 17, wherein the articulable bending section of the flexible robotic endoscope is actuated by the second instrument driving mechanism.

19. The suturing instrument of claim 1, wherein the rotation mechanism comprises a toggle to switch the orientation of the needle when the needle reaches a fully retracted position of a cycle.

20. The suturing instrument of claim 1, wherein a flag feature fixedly coupled to the needle traverses along the one or more channels to switch the orientation of the needle about the axial axis of the needle.

* * * * *